United States Patent
Overton et al.

(10) Patent No.: US 10,004,394 B2
(45) Date of Patent: Jun. 26, 2018

(54) RETINAL ILLUMINATION SYSTEM

(71) Applicant: LumenDevices, LLC, Dallas, TX (US)

(72) Inventors: Kenneth J. Overton, Princeton, TX (US); Rajiv Anand, Dallas, TX (US)

(73) Assignee: LUMENDEVICES, LLC, Dallas, TX (US)

( * ) Notice: Subject to any disclaimer, the term of this patent is extended or adjusted under 35 U.S.C. 154(b) by 24 days.

(21) Appl. No.: 14/984,121

(22) Filed: Dec. 30, 2015

(65) Prior Publication Data
US 2017/0049313 A1 Feb. 23, 2017

Related U.S. Application Data

(60) Provisional application No. 62/207,601, filed on Aug. 20, 2015.

(51) Int. Cl.
| | | |
|---|---|---|
| A61B 3/10 | (2006.01) | |
| A61B 3/02 | (2006.01) | |
| A61B 3/00 | (2006.01) | |
| A61B 17/02 | (2006.01) | |
| A61F 9/007 | (2006.01) | |

(52) U.S. Cl.
CPC ........ *A61B 3/0008* (2013.01); *A61B 17/0231* (2013.01); *A61F 9/007* (2013.01)

(58) Field of Classification Search
CPC ... G02B 6/0006; G02B 23/2469; A61F 9/007; A61F 9/00736; A61F 9/0017; A61F 9/0026; A61B 50/20; A61B 50/30; A61B 50/33; A61B 46/00; A61B 3/0008; A61B 17/0231; A61B 17/0218; A61B 17/3423; A61B 1/0684; A61B 1/07; A61B 1/313; A61B 3/00736

USPC ........ 351/221, 243, 211, 246; 362/551, 555; 600/3, 236, 425; 604/20
See application file for complete search history.

(56) References Cited

U.S. PATENT DOCUMENTS

| | | | |
|---|---|---|---|
| 5,318,560 A | 6/1994 | Blount et al. | |
| 5,725,514 A | 3/1998 | Grinblat et al. | |
| 6,786,628 B2 | 9/2004 | Steen et al. | |
| 7,815,312 B2 | 10/2010 | Matsumura et al. | |
| 8,061,840 B2 | 11/2011 | Mizuochi | |
| 8,172,834 B2 | 5/2012 | Bhadri et al. | |
| 9,089,364 B2 | 7/2015 | Bhadri et al. | |
| 2007/0019160 A1 | 1/2007 | Kleen et al. | |
| 2007/0195521 A1* | 8/2007 | Rosiello | F21L 4/00 362/202 |
| 2009/0146583 A1* | 6/2009 | Bhadri | A61B 3/0008 315/294 |
| 2011/0110114 A1* | 5/2011 | Papac | A61B 90/30 362/555 |

(Continued)

FOREIGN PATENT DOCUMENTS

WO 2014/066777 A1 5/2014

*Primary Examiner* — Mustak Choudhury
(74) *Attorney, Agent, or Firm* — Hall Estill Attorneys at Law; Tyler J. Mantooth

(57) ABSTRACT

A solid state illuminator can be used for a variety of surgery procedures, such as retinal surgery. A retinal illumination system my have at least one light emitting diode located on a substrate with the substrate positioned on an eye of a patient. A light pipe can continuously extend from the light emitting diode into a sclera of the eye via a cannula. A system controller may be configured to activate the light emitting diode to illuminate an interior of the eye.

19 Claims, 3 Drawing Sheets

(56) References Cited

U.S. PATENT DOCUMENTS

| | | | | |
|---|---|---|---|---|
| 2011/0149591 A1* | 6/2011 | Smith | ............... | A61B 3/0008 362/555 |
| 2011/0282160 A1* | 11/2011 | Bhadri | ............... | A61B 3/0008 600/236 |
| 2014/0024951 A1* | 1/2014 | Herzlinger | ......... | A61B 5/0084 600/478 |
| 2014/0232985 A1 | 8/2014 | Yates | | |

\* cited by examiner

RETINAL ILLUMINATION SYSTEM

RELATED APPLICATION

The present application makes a claim of domestic priority to U.S. Provisional Patent Application No. 62/207,601 filed Aug. 20, 2015, the contents of which are hereby incorporated by reference.

SUMMARY

A retinal illumination system, in accordance with various embodiments, has at least one light emitting diode located on a substrate and the substrate positioned on an eye of a patient. A light pipe continuously extends from the light emitting diode and substrate into the retina and vitreous of patient's eye through a cannula. A system controller activates the at least one light emitting diode to illuminate an interior of the patient's eye.

DETAILED DESCRIPTION

To illuminate a surgical site, large and expensive operating room equipment generates light that is transmitted to a hand piece manipulated by the surgeon. Such manual control of the illuminating means requires the surgeon to dedicate one hand to positioning and manipulating the light delivery instrument while using the other hand to perform the surgery, which can be characterized as unimanual surgery.

In retinal surgery, a surgeon accesses the retina with surgical equipment inserted through one or more cannulas that extend through the sclera of a patient's eye to the vitreous body. Light emitted into the eye allows the surgeon to view the surgical site and instrument manipulation through a microscope directed through the cornea and lens from the outside of the eye. The narrow light field produced by common illuminating means forces the surgeon to manually manipulate the large illumination equipment while trying to perform precise surgery.

Hence, various embodiments of the present disclosure are directed to a retinal illumination system that provides a wide angle, broad illumination of the interior of a patient's eye via one or more entry points. A retinal illumination system can eliminate the unimanual surgery by freeing both hands of the surgeon from the task of manipulation of the illumination means. By configuring illuminating means to be small and light, the retinal illumination system is lightweight and provides a minimally invasive package that can be positioned on the patient. In some embodiments, the retinal illumination system is disposable and constructed as a single-use device that employs multiple different illuminating means.

Figure 1:
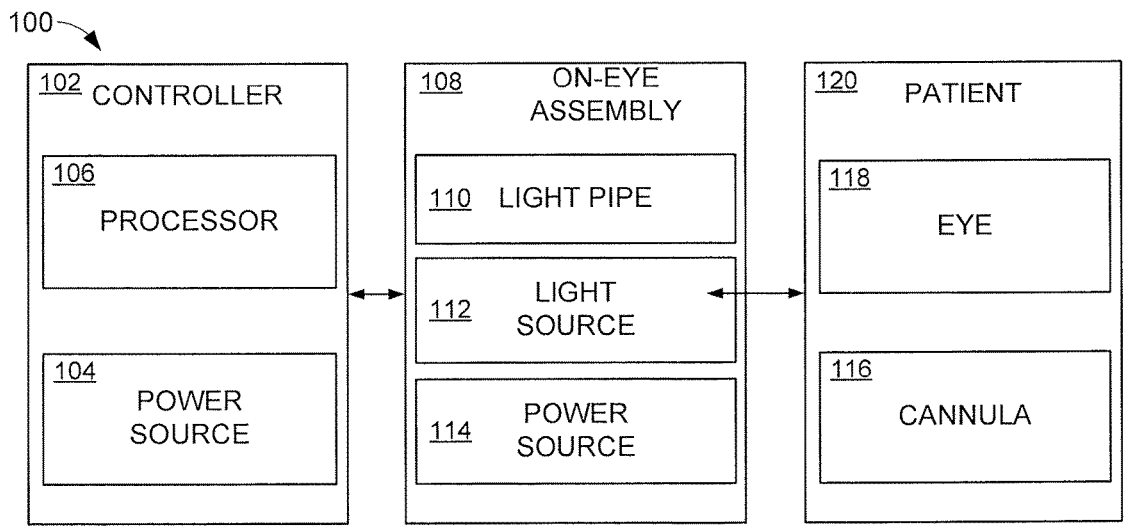
FIG. 1 is a block representation of an example retinal illumination system in accordance with various embodiments.

FIG. 1 is a block representation of an example retinal illumination system 100 arranged in accordance with assorted embodiments. The system 100 can have a controller 102 that utilizes at least a power source 104 and processor 106, such as microcontroller, microprocessor, or application specific integrated circuit (ASIC). The various aspects of the controller 102 may be packaged together into a common housing or individually packaged and connected via wired and/or wireless electrical pathways.

The controller 102 is connected to at least one on-eye assembly 108 that consists of a light pipe 110, light emitting source 112, and a power source 114. The on-eye assembly 108 can have one or more rigid or flexible substrates on which the light-emitting source 112 is mounted. The light-emitting source 112, in some embodiments, is one or more light emitting diodes (LED) that can efficiently be packaged in the on-eye assembly 108 without unduly adding weight, complexity, or cost to the system 100. It is noted that the number, type, and position of the light emitting source 112 is not limited to a single source or outlet. For example, multiple different light emitting sources 112 may concurrently be packaged into an on-eye assembly 108 and direct light to a common, or multiple different, light pipes 110.

Regardless of the configuration of the on-eye assembly 108, inserting the light pipe 110 into a cannula 116 can access the eye 118 of patient 120. The lightweight construction of the on-eye assembly 108 allows the light-emitting source 112 to be physically positioned atop the cannula 116, which optimizes the efficiency of light generation while allowing hands-free, bimanual, surgery. The packaged configuration of the light-emitting source 112 and light pipe 110 on the patient's eye 118 further allows some, or all, of the retinal illumination system 100 to be one-time use and disposable, which can provide increased sanitation and accuracy for retinal surgery compared to reused illumination components.

Figure 2:
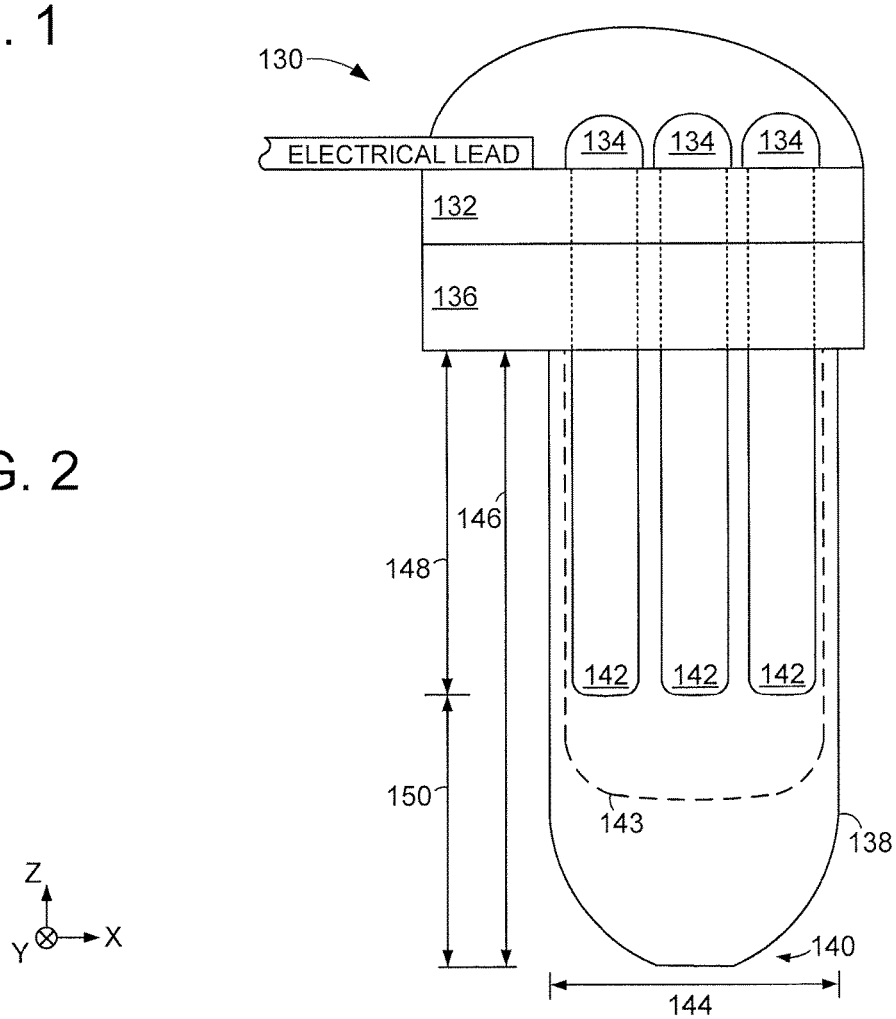
FIG. 2 illustrates a block representation of an example on-eye assembly capable of being utilized by the retinal illumination system of FIG. 1.

FIG. 2 displays a cross-sectional line representation of an example on the eye assembly 130 that may be utilized in the retinal illumination system 100 of FIG. 1 in accordance with some embodiments. The on-eye assembly 130 has a substrate 132 on which a plurality of LEDs 134 are mounted. It is noted that the substrate 132 can employ any number of light-emitting sources of similar, or dissimilar, types, light intensities, and sizes. The substrate 132 may further support a power source, such as a battery or capacitor, local memory, such as a solid-state non-volatile local data storage, and a processing means, such as a microcontroller and/or integrated circuit.

A land 136 is positioned between the substrate 132 and a cannula, such as cannula 116 of FIG. 1, and provides a suspension and platform to structurally support the electronics of the substrate 132. The land 136 can be configured of a flexible material, such as silicon, rubber, gel, or elastomer, that provides a positive stop for insertion of the light pipe 138 into the cannula. In some embodiments, the land 136 can be interchanged by a surgeon to determine the depth of the light pipe 138 into the cannula, which corresponds with the shape of light being emitted into the patient's eye.

Light can be translated from the LED(s) 134 to a pipe tip 140 via one or more cables 142, which may be fiber optic or other mirrored structure. Each LED 134, in some embodiments, has a corresponding cable 142, as shown in FIG. 2. However, multiple LEDs 134 can collectively emit light into a single cable, as shown by segmented line 143, or the light pipe 138 itself with portions of the light pipe 138 shaped and/or coated to transmit light in a predetermined manner to the pipe tip 140. That is, the light pipe 138 may have a uniform or varying diameter 144 throughout its length 146 and may be silvered or mirrored in sections to provide a broad light dispersion from the pipe tip 140 instead of a narrow light dispersion pattern found in a cable 142.

The on-eye assembly 130 may be constructed with the various cables 142 being similar, or dissimilar, lengths 148 that are separated from the pipe tip 140 by a predetermined distance 150, such as 2 mm, that operates in concert with the shape of the pipe tip 140 to broadcast light in a manner that illuminates a majority of a patient's retina. It is contemplated that the substrate 132 may present one or more articulation features, such as buttons, knobs, handles, and/or protrusions, that allows a surgeon to alter and/or manipulate the on-eye assembly 130 at will.

As a non-limiting example, engagement of an articulation feature may alter the position of one or more cables 142 relative to the pipe tip 140 or may alter the color, wavelength, or light dispersion pattern from the on-eye assembly 130. The ability to construct the light pipe 138 with a precise shape and length 146 allows the on-eye assembly 130 to fit wholly within the land 136 and cannula, which stabilizes the generated light and allows the surgeon to employ bimanual movements. It is noted that the light pipe 138 can comprise: a single optical fiber, a number of optical fibers of the same, or different, diameters that are bonded together to form a multi-channel light piper, or a number of optical fibers of the same, or different diameters that are not bonded together. The diverse possible light pipe configurations can allow individual light fibers to splay apart once in the eye to provide multiple separate light sources.

Figure 3A:
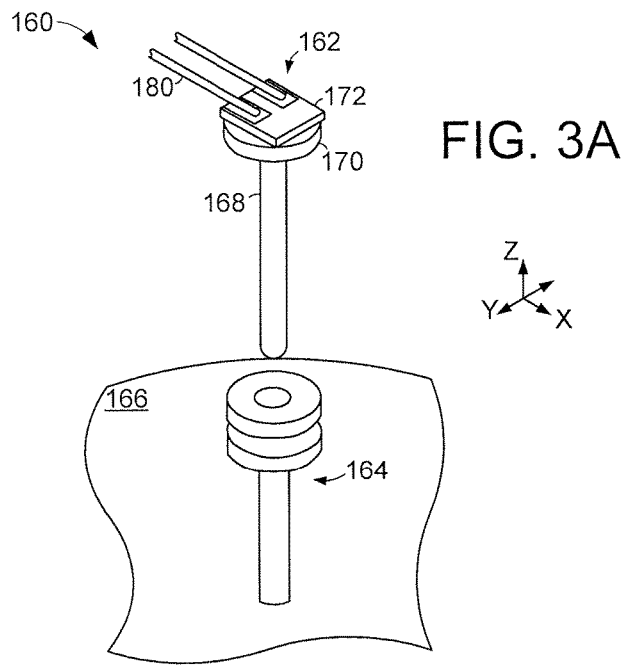
FIGS. 3A and 3B respectively show perspective and cross-sectional views of a portion of the example retinal illumination system of FIG. 1.
Figure 3B:
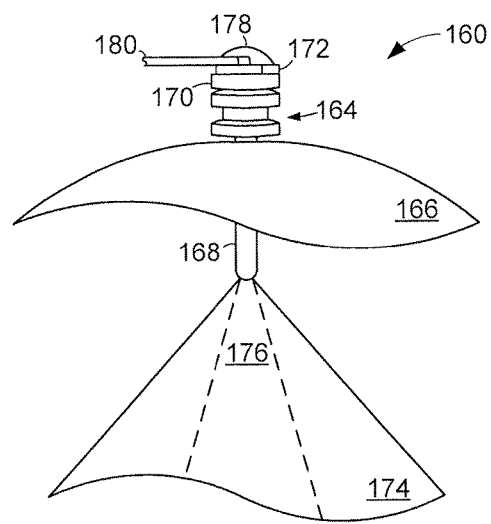

FIGS. 3A and 3B respectively illustrate different line representations of portions of an example retinal illumination system 160 that is constructed and operated in accordance with assorted embodiments. In FIG. 3A, an on-eye assembly 162 is separated from a cannula 164 that extends through the sclera of a patient's eye 166. The separation of the on-eye assembly 162 from the cannula 164 exposes how the light pipe 168 is shaped to easily be inserted, and removed, from the cannula 164 without altering the cannula 164 or the eye 166. It is further noted that the land 170 is attached to the substrate 172, but such configuration is not required as the land 170 may be a separate component from the substrate 172 that can be positioned atop the cannula 164 independent of the light pipe 168.

Upon insertion of the light pipe 168 into the cannula 164, as shown in FIG. 3B, the land 170 provides a structural platform for the substrate 172. The land 170 may also provide heat mitigating functions by being constructed of a heatsink material, such as rubber, or be shaped to inhibit the transmission of heat from the substrate 172 to the patient's eye 166, such as with fins or coatings. Activation of the electronics packaged on the substrate 172 produces a predetermined light dispersion 174 that may be static or dynamic, as represented by segmented dispersion 176.

In accordance with various embodiments, a cap 178 seals the substrate 172 and comprises a flexible or rigid material to protect the electrical components mounted on the substrate 172 from environmental conditions as well as protecting the patient from electrical discharge. The pre-packaging of the substrate 172 with the cap 178 allows the on-eye assembly 162 to be sanitary and disposable. It is noted that the cap 178 can be partially or completely penetrated by one or more electrical components 180, such as an electrical wire lead, antenna, button, or knob.

Figure 4:
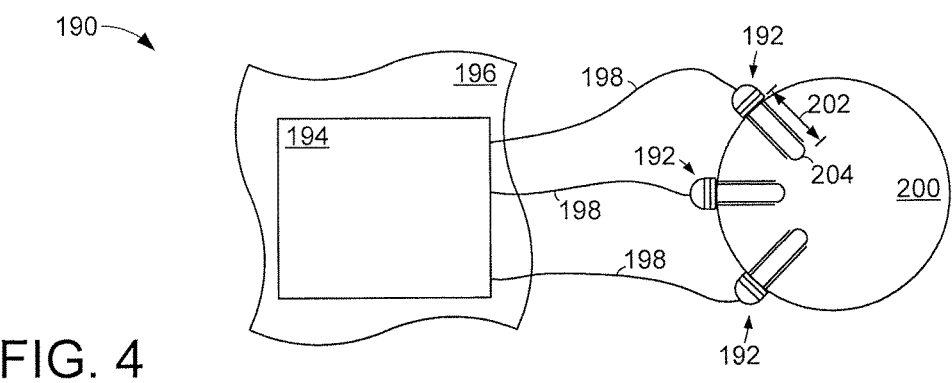
FIG. 4 displays a block representation of a portion of an example retinal illumination system configured in accordance with various embodiments.

FIG. 4 is a line representation of an example retinal illumination system 190 configured with multiple separate on-eye assemblies 192 connected to a common system controller 194 in accordance with some embodiments. The system controller 194 is constructed with a size and weight conducive to placement on a patient 196, such as the gown of the patient 196. The system controller 194 may be electrically connected to the respective on-eye assemblies 192 via wires 198, as shown, or via wireless pathways facilitated by wireless transmission and reception components.

The lightweight and small size of the respective on-eye assemblies 192 allow multiple separate assemblies 192 to be concurrently engaged with a single eye. Such simultaneous engagement of different on-eye assemblies 192 provides the ability to tune the delivery of light into the patient's eye 200. For example, different on-eye assemblies 192 can have different physical configurations and/or different light emitting characteristics to collectively provide optimized illumination of a patient's retina. A physical configuration may be the diameter, shape, or length 202 of a light pipe 204. A light emitting characteristic may be the wavelength of light emitted and/or pattern of light dispersion.

The ability to concurrently deliver different lighting configurations can minimize long-term retinal exposure and allow certain features of the retina to be highlighted with specific wavelengths. For instance, a first on-eye assembly 192 can provide global illumination with a wide dispersion pattern while a second on-eye assembly 192 generates spot illumination with a more narrow light dispersion pattern. The capability of the system controller 194 to change the wavelength, brightness, color, and pattern of light generated by the respective on-eye assemblies 192 allows for individual and collective activation of the on-eye assemblies 192 that cannot be achieved with a single light source that operates at a fixed wavelength.

Figure 5:
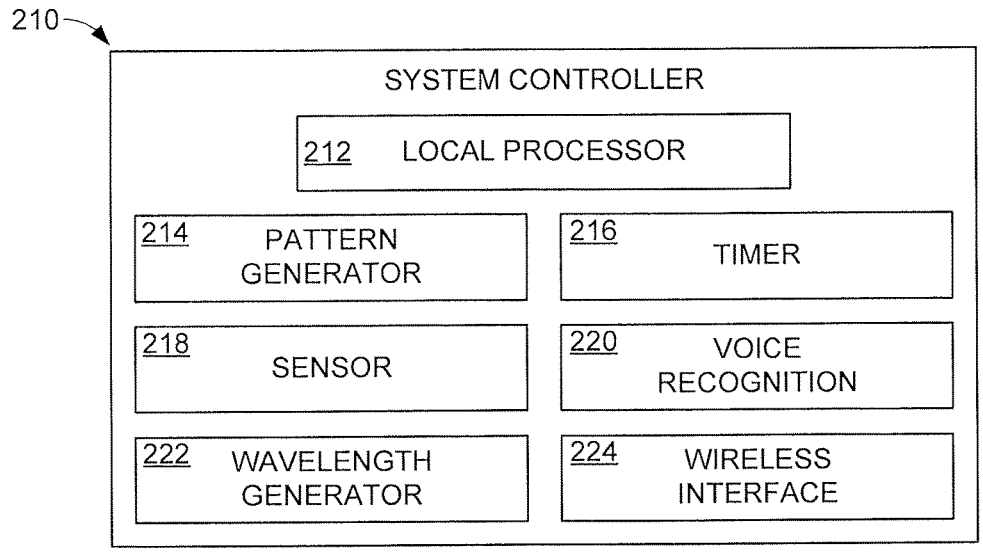
FIG. 5 conveys a block representation of an example controller capable of being used in the retinal illumination system of FIG. 1.

FIG. 5 illustrates a block representation of an example system controller 210 capable of being employed by a retinal illumination system in accordance with various embodiments. The controller 210 can have any number of operational capabilities enabled by physical components, such as LEDs, integrated circuits, and power sources mounted on an on-eye assembly, and/or software executed by a local processor 212.

While not limiting, the system controller 210 can have a pattern generator 214 that can orchestrate different on-eye assemblies to illuminate a patient's retina in a manner conducive to surgery on the retina. As an example, the pattern generator 214 may direct light with different wavelengths, brightness, and/or color to be produced concurrently or at different times to highlight particular portions of the retina. A timer 216 may be utilized in conjunction with the pattern generator 214 to produce light at predetermined times during surgery. For instance, the timer 216 may be automatically initiated by activation of a light source or may be activated in response to prompting by a surgeon.

The system controller 210 may have one or more sensors 218, such as optical, proximity, and acoustic sensors, that monitor the condition of the patient, surgery, environment, and light generated. That is, a sensor 218 can continually, routinely, or randomly verify the accuracy, or detect an error, in the light being generated by an on-eye assembly. A sensor 218 may also autonomously detect environmental conditions, such as temperature, humidity, and moisture, and alter the generation of light, such as changing wavelength or brightness, in response to the detected condition. The autonomous detection and alteration of light generation can provide increased safety and precision for retinal surgery.

Although a retinal illumination system can be operated via manual manipulation, the system controller 210 can have one or more voice recognition 220 components, such as a microphone, that allow hands-free manipulation of light illumination. That is, instead of having to physically touch the controller 210 or an on-eye assembly to alter how light illuminates a patient's retina, the voice recognition 220 of the controller can detect, decode, and translate commands from a surgeon into control of light generation by the system. For example, the surgeon can verbally activate a single on-eye assembly, change the wavelength being generated, and alter a pattern of light being emitted by multiple different on-eye assemblies.

A wavelength generator 222, such as an oscillator, can generate various different wavelengths. It is noted that multiple different wavelength generators 222 may be present in the system controller 210 and operate concurrently to produce a variety of wavelengths concurrently. The system controller 210 may also have a wireless interface 224 that provides access to a remote and/or local network via appropriate protocol.

The ability to wirelessly interact with a remote host, such as a node, processor, or server, allows the system controller 210 to have a reduced physical size as remote computing aspects, such as memory, software, and data processing, can be handled remotely. Connection with a remote host can further allow the system controller 210 to be less sophisticated in terms of computing power and data capacity, which decreases the cost of the controller 210 and allows the retinal illumination system to be a single-use, disposable device.

It is contemplated that the system controller 210 and any connected on-eye assemblies can be practiced in an unlimited variety of environments and for a diverse variety of surgical procedures. In accordance with some embodiments, the retinal illumination system of FIGS. 1-5 is employed to execute the example retinal illumination routine 230 of FIG. 6. Initially, the routine 230 can position one or more cannula(s) in the eye of a patient in step 232 with each cannula continuously extending through the sclera of the eye and into the vitreous body, which may be facilitated by using a trocar in order to provide multiple access points.

An on-eye assembly is then inserted into at least one cannula in step 234. The insertion of step 234 can involve separately, or concurrently, placing a land between the cannula and a substrate of the assembly. It is noted that step 234 may insert a number of different on-eye assemblies with different physical configurations and light generating capabilities into separate cannulas, as generally illustrated in FIG. 4. Each on-eye assembly is then electrically connected to a system controller in step 236 that is placed on the patient. That is, step 236 can physically connect wires to the respective on-eye assemblies or establish a wireless connection before, during, or after the system controller is placed in contact with the patient.

Step 238 subsequently activates at least one on-eye assembly to generate light and illuminate a portion of the retina of the patient. The light generated in step 238 can be activated by manual selection or verbal command and continue for any amount of time. However, the light generated in step 238 may be altered in step 240 in response to a direct or indirect stimulus. For instance, the wavelength, brightness, color, number of active on-eye assemblies, and/or pattern of light generated in step 238 may be altered in step 240 upon automatic detection of a change in condition, such as a timer expiring or temperature threshold being met, or upon selection by the surgeon.

With the ability for the retinal illumination system to be actively selected or indirectly react to sensed conditions, retinal surgery can be more accurate and precise as sophisticated combinations of light patterns, colors, and wavelengths can sequentially and simultaneously highlight different portions of the retina.

Figure 6:
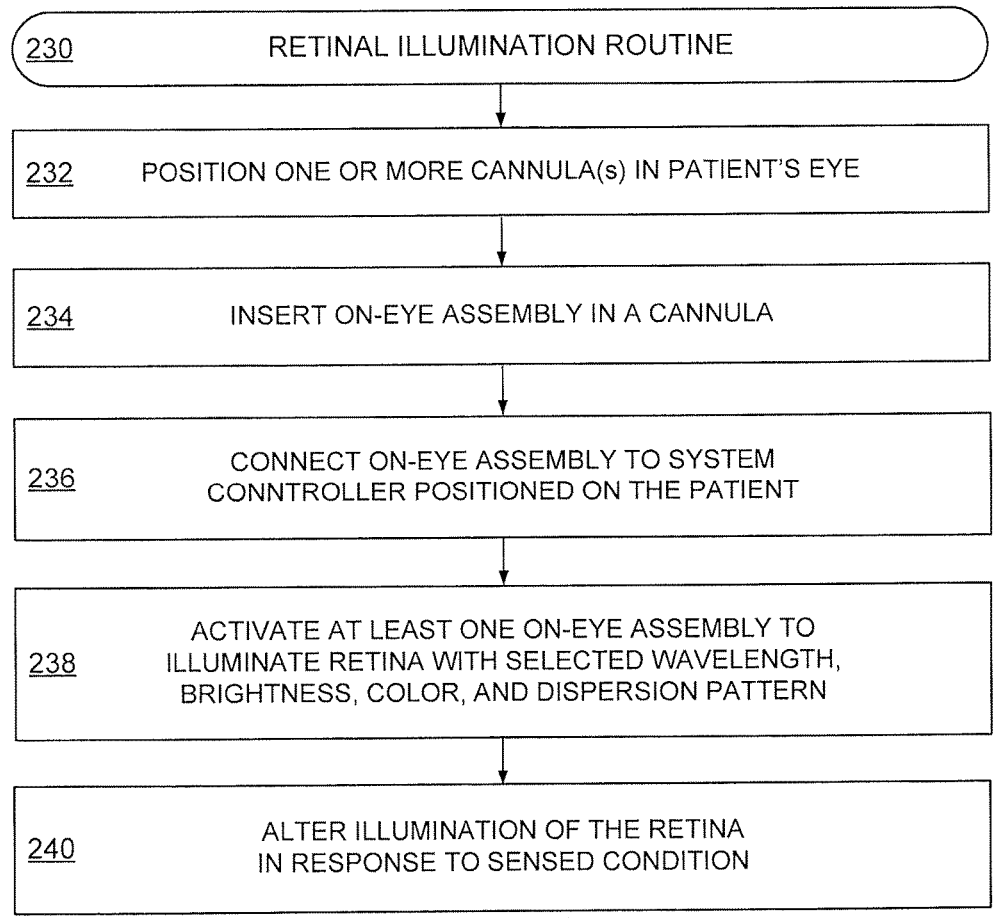
FIG. 6 provides a flowchart of an example retinal illumination routine carried out with various embodiments of the retinal illumination system of FIG. 1.

While the retinal illumination routine 230 can be conducted alone and as illustrated in FIG. 6, the routine 230 is not limited to the particular displayed aspects. Hence, any step of routine 230 can be altered or removed just as any step or decision can be added. As an example, an additional decision can be added to routine 230 to determine the quality of light being generated by the on-eye assembly, which may detect errors, failed connections, or misalignment of a light pipe and cannula.

Through the various embodiments of a retinal illumination system, a wide angle, broad illumination of the interior of the eye can be generated with one or more assemblies that locate a light source, and in some instances a power source, atop the eye of the patient. The configuration of the on-eye assembly and a system controller eliminates the need for a surgeon to actively manipulate an illuminator, which provides bimanual surgery. It can be appreciated that the various aspects allow the retinal illumination system to be small and light that provides a minimally intrusive package that may be constructed for a low cost as a single-use, disposable unit.

What is claimed is:

1. An apparatus comprising:
   a first light emitting diode (LED) located on a substrate, the substrate positioned on an eye of a patient;
   a light pipe continuously extending from the first LED into a sclera of the eye via a cannula, the substrate separated from the cannula by a land feature, the land feature being interchangeable and concurrently contacting the cannula and the substrate to determine a depth of the light pipe into the cannula;
   a first optical cable continuously extending from the first LED through the substrate and the land feature into the light pipe;
   a system controller to activate the first LED to illuminate an interior of the eye; and
   the land feature and substrate are solely supported by the cannula.

2. The apparatus of claim 1, wherein a second LED is positioned on the substrate and a second optical cable continuously extends from the second LED through the substrate and land feature into the light pipe.

3. The apparatus of claim 2, wherein the first and second optical cables are physically separated in the light pipe.

4. The apparatus of claim 2, wherein the light pipe houses a single fiber optic cable continuously extending from the first and second LEDs to a pipe tip.

5. The apparatus of claim 1, wherein a power source is attached to the substrate.

6. The apparatus of claim 1, wherein a cap contacts the substrate and seals a first side of the substrate.

7. The apparatus of claim 1, wherein the first optical cable has a first length and the second optical cable has a second length, each length measured from the land feature, the first length being different from the second length.

8. The apparatus of claim 1, wherein the light pipe has body diameter along a body portion and a pipe tip having a tip diameter, the tip diameter being smaller than the body diameter.

9. The apparatus of claim 1, wherein a portion of the light pipe is coated to decrease light transmission through a body portion of the light pipe.

10. The apparatus of claim 1, wherein the system controller is positioned on the patient and is only connected to the substrate via an electrical lead.

11. An apparatus comprising:
a first cannula extending through a sclera of the eye;
a second cannula extending through the sclera of the eye;
a first assembly positioned on the first cannula, the first assembly comprising a first substrate, at least one light emitting diode (LED), and a first light pipe, the first substrate separated from the first cannula by a first land feature, the first land feature being interchangeable and concurrently contacting the first cannula and the first substrate to determine a depth of the first light pipe into the first cannula, the first assembly solely supported by the first cannula;
a second assembly positioned on the second cannula, the second assembly comprising a second substrate, at least one light emitting diode (LED), and a second light pipe, the second substrate separated from the second cannula by a second land feature, the second land feature being interchangeable and concurrently contacting the second cannula and the second substrate to determine a depth of the second light pipe into the second cannula, the second assembly solely supported by the second cannula; and
a system controller electrically connected to each assembly to illuminate an interior of the eye.

12. The apparatus of claim 11, wherein the first light pipe has a greater length than the second light pipe, each length measured perpendicular to the substrate.

13. The apparatus of claim 11, wherein a plurality of LEDs are present in the first assembly and a single LED is present in the second assembly.

14. The apparatus of claim 11, wherein the first and second cannula are separate and positioned in different portions of the eye.

15. The apparatus of claim 11, wherein the first light pipe is shaped differently than the second light pipe.

16. A method comprising:
positioning a first cannula in an eye of a patient;
positioning a second cannula in the eye, each cannula extending through a sclera of the eye;
inserting a first assembly into the first cannula, the first assembly comprising a first substrate, at least one light emitting diode (LED), and a first light pipe, the first substrate separated from the first cannula by a first land feature, the first land feature being interchangeable and concurrently contacting the cannula and the substrate to determine a first depth of the first light pipe into the first cannula;
inserting a second assembly into the second cannula, the second assembly comprising a second substrate, at least one light emitting diode (LED), and a second light pipe, the second substrate separated from the second cannula by a second land feature, the second land feature being interchangeable and concurrently contacting the second cannula and the second substrate to determine a second depth of the second light pipe into the second cannula;
illuminating the eye with at least one of the first and second assemblies via a system controller electrically connected to each assembly; and
conducting bimanual surgery on the patient without touching either the first or second assemblies.

17. The method of claim 16, wherein the system controller alters operation of the first assembly in response to a sensed change in condition within the eye.

18. The method of claim 16, wherein the system controller emits different wavelengths concurrently from the respective assemblies at different light dispersion patterns.

19. The method of claim 16, wherein the system controller alters a light from the first assembly in response to a verbal command from a surgeon, the alteration of the light conducted without a activation or manipulation by a hand of the surgeon.

* * * * *